(12) United States Patent
Nemoto et al.

(10) Patent No.: US 8,841,284 B2
(45) Date of Patent: Sep. 23, 2014

(54) COMPOUND HAVING NEURITE-OUTGROWING ACTIVITY

(75) Inventors: Hideo Nemoto, Toyama (JP); Yuji Matsuya, Imizu (JP)

(73) Assignee: Lead Chemical Co., Ltd, Toyama (JP)

( * ) Notice: Subject to any disclaimer, the term of this patent is extended or adjusted under 35 U.S.C. 154(b) by 0 days.

(21) Appl. No.: 13/389,105

(22) PCT Filed: Jul. 21, 2009

(86) PCT No.: PCT/JP2009/063063
§ 371 (c)(1),
(2), (4) Date: Apr. 6, 2012

(87) PCT Pub. No.: WO2011/010364
PCT Pub. Date: Jan. 27, 2011

(65) Prior Publication Data
US 2012/0190841 A1  Jul. 26, 2012

(51) Int. Cl.
*A61K 31/585* (2006.01)
*C07J 17/00* (2006.01)
*C07J 51/00* (2006.01)

(52) U.S. Cl.
CPC .............. *A61K 31/585* (2013.01); *C07J 51/00* (2013.01); *C07J 17/00* (2013.01)
USPC ........... 514/175; 540/106; 540/108; 540/109; 540/112; 540/115

(58) Field of Classification Search
USPC ........... 514/175; 540/106, 108, 109, 112, 115
See application file for complete search history.

(56) References Cited

FOREIGN PATENT DOCUMENTS

| JP | A-2006-176428 | 7/2006 |
| WO | WO 2007/094166 A1 | 8/2007 |
| WO | WO 2008/102716 A1 | 8/2008 |

OTHER PUBLICATIONS

Matsuya et al., "Synthesis and Antitumor Activity of the Estrane Analogue of OSW-1," *Eur. J. Org. Chem.*, 2005, pp. 803-808.
Yamakawa et al., "Ninchisho Chiryoyaku Kaihatsu wo Mezashita sominone Oyobi Ruien Kagobutsu no Gosei," *Dai 38 Kai Book of Abstracts Congress of Heterocyclic Chemistry*, Oct. 10, 2008, pp. 213-214 (with abstract).
Veleiro et al., "A Phenolic Withanolide from Jaborosa Leucotricha," *Phytochemistry*, vol. 31, No. 7, 1992, pp. 2550-2551.
Sinha et al., "Structures of Withametelin and Isowithametelin, Withanolides of Datura Metel Leaves," *Tetrahedron*, vol. 45, No. 7, 1989, pp. 2165-2176.
Oct. 27, 2009 Written Opinion issued in International Patent Application No. PCT/JP2009/063063.
Oct. 27, 2009 International Search Report issued in International Patent Application No. PCT/JP2009/063063 (with translation).

*Primary Examiner* — Brenda Coleman
(74) *Attorney, Agent, or Firm* — Oliff PLC

(57) ABSTRACT

There is provided a novel compound having neurite-outgrowing activity that is useful for the prevention or the treatment of a neurodegenerative disease. A compound of Formula (I)

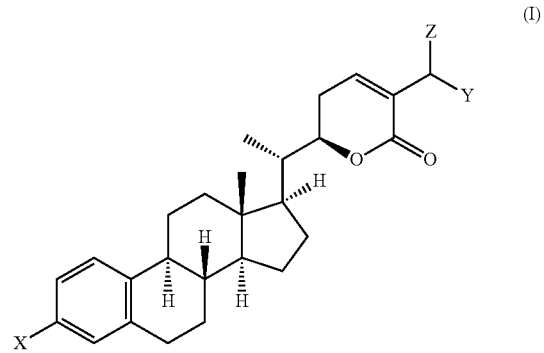

[where X is OR or $NR_1R_2$, Y is OH, $NR_3R_4$, —NHC(=NH)$NHR_5$, or —NHC(=NH)$R_5$, and Z is a hydrogen atom, a linear or branched $C_{1-5}$ alkyl group, or a 5- or 6-membered ring aryl group optionally having 1 or 2 nitrogen atom(s), sulfur atom(s), or oxygen atom(s)], or a pharmaceutically or veterinary-medically acceptable salt of the compound.

4 Claims, 6 Drawing Sheets

COMPOUND HAVING NEURITE-OUTGROWING ACTIVITY

TECHNICAL FIELD

The present invention relates to a novel compound having neurite-outgrowing activity that is useful for the prevention or the treatment of a neurodegenerative disease.

BACKGROUND ART

A neuron has two types of neurites, i.e., a dendrite that accepts information from another neuron and an axon that sends out information to another neuron. The extinction of neurons or the atrophy of neurites due to various causes inhibits a normal information transfer between neurons, so that various diseases are caused depending on the region of the nervous system that has been damage. Specific examples of the diseases caused by damage of the central nervous system (brain, spinal cord) include Parkinson's disease, Alzheimer's disease, and amyotrophic lateral sclerosis and specific examples of the diseases caused by damage of peripheral nerves include polyneuropathy and Guillain-Barré syndrome. Particularly, the disease of the central nervous system is progressive, and an effective treatment technique for the disease has not been developed yet. Although a neurotrophic factor-like agonist is studied as a therapeutic agent for the disease of the central nervous system, such an agonist has mainly neuroprotective effect and the neurite-outgrowing activity of the agonist under neurodegenerative circumstances has not been clearly shown. As the treatment for the neurodegenerative disease, it is necessary not only to inhibit the death of a neuron, but also to outgrow a neurite of a residual neuron to normalize the information transfer between neurons, so that the development of a therapeutic agent for a neurodegenerative disease that has both a neuron death-inhibiting activity and a neurite-outgrowing activity is desired.

On the other hand, it is known that sominone, which is a compound extracted from Indian ginseng, has an excellent neurite-outgrowing activity (Patent Document 1) and that withanoside IV has an outgrowing activity of an axon of a spinal cord cell (Patent Document 2).

RELATED-ART DOCUMENT

Patent Document

Patent Document 1: Japanese Patent Application Publication No. JP-A-2006-176428
Patent Document 2: International Publication No. WO 2007/094166 pamphlet

SUMMARY OF THE INVENTION

Problem to be Solved by the Invention

In view of the above, the present invention provides a novel compound having both a neuron death-inhibiting activity and a neurite-outgrowing activity, and a therapeutic agent for a neurodegenerative disease containing the compound.

Means for Solving the Problem

As a result of assiduous research for solving the above problems, the inventors of the present invention have found a novel compound exhibiting a neurite-outgrowing activity in a rat fetus cerebral cortex neuron and exhibiting an axon-outgrowing activity in a rat spinal cord dorsal root ganglion (spinal cord neuron), and have completed the present invention.

From the above description, it can be expected that a medicine containing the compound of the present invention makes possible the treatment of a neurodegenerative disease caused by the death of a neuron or the atrophy of a neurite.

That is, the present invention relates to (1) a compound of Formula (I)

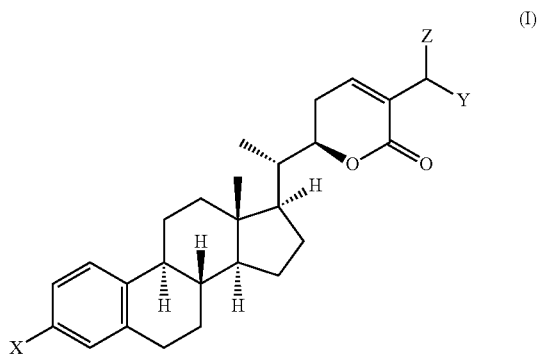

[where X is OR (where R is a hydrogen atom, a linear or branched $C_{1-5}$ alkyl group, or a linear or branched $C_{1-5}$ acyl group) or $NR_1R_2$ (where $R_1$ and $R_2$ are independently a hydrogen atom, a linear or branched $C_{1-5}$ alkyl group, or a linear or branched $C_{1-5}$ acyl group); Y is OH, $NR_3R_4$ (where $R_3$ and $R_4$ are independently a hydrogen atom or a linear $C_{1-3}$ alkyl group, or $R_3$ and $R_4$ together form, with a nitrogen atom to which they are bonded, a 5-membered ring or a 6-membered ring optionally containing a nitrogen atom or an oxygen atom as a ring constituting atom), —NHC(=NH)NHR$_5$, or —NHC(=NH)R$_5$ (where R$_5$ is a linear or branched $C_{1-5}$ alkyl group); and Z is a hydrogen atom, a linear or branched $C_{1-5}$ alkyl group, or a 5- or 6-membered ring aryl group optionally having 1 or 2 nitrogen atom(s), 1 or 2 sulfur atom(s), or 1 or 2 oxygen atom(s)], or a pharmaceutically or veterinary-medically acceptable salt of the compound;

(2) a medicine containing the compound as described in (1) or a pharmaceutically or veterinary-medically acceptable salt of the compound;

(3) a prophylactic agent or a therapeutic agent for a neurodegenerative disease containing the compound as described in (1) or a pharmaceutically or veterinary-medically acceptable salt of the compound; and (4) a neurite-outgrowing agonist containing the compound as described in (1) or a pharmaceutically or veterinary-medically acceptable salt of the compound.

Effects of the Invention

The compound of the present invention is a novel compound having a peculiar structure in which one ring of fused rings is aromatized. The compound of the present invention has a neurite-outgrowing activity (axon and dendrite) and a neuron death-inhibiting activity, so that the compound can be advantageously used, for example, as an active ingredient of a therapeutic agent for a neurodegenerative disease such as Alzheimer's disease, spinal cord injury, and amyotrophic lateral sclerosis.

MODES FOR CARRYING OUT THE INVENTION

Figure 1:
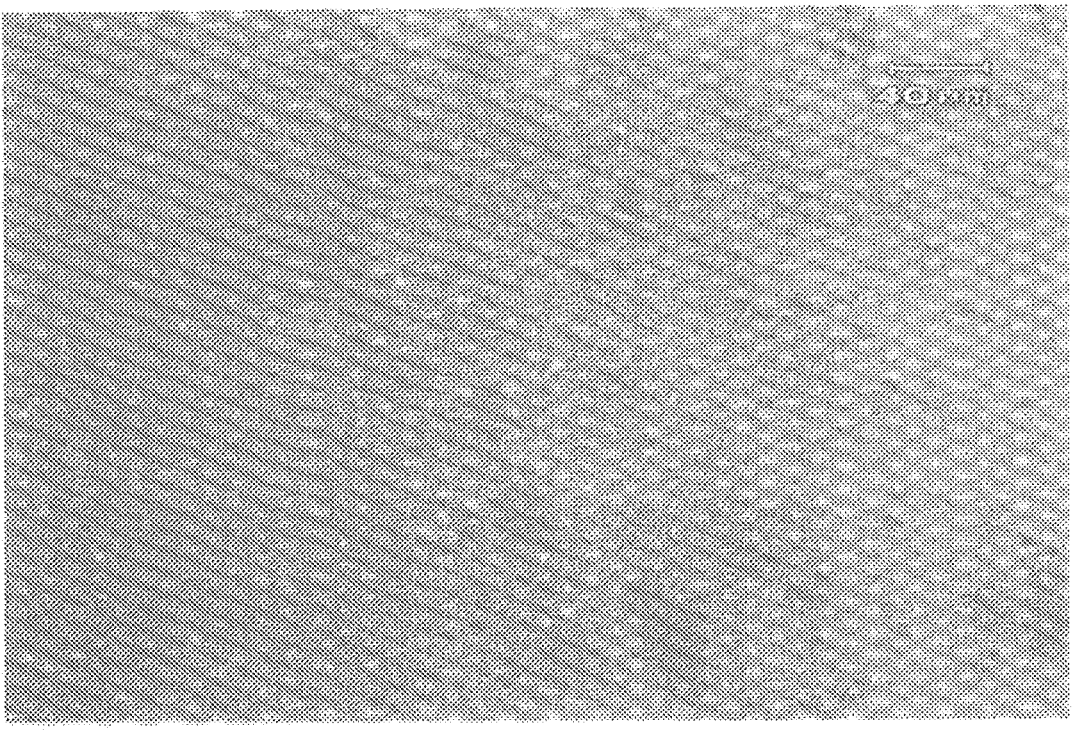
FIG. 1 is a photograph of a rat fetus cerebral cortex neuron on the second day of the culture in a basal medium (additive-free) (in a poly-L-lysine-coated culture vessel).

The compound of the present invention or a pharmaceutically or veterinary-medically acceptable salt of the compound has a structure of Formula (I):

[where X is OR (where R is a hydrogen atom, a linear or branched $C_{1-5}$ alkyl group, or a linear or branched $C_{1-5}$ acyl group) or $NR_1R_2$ (where $R_1$ and $R_2$ are independently a hydrogen atom, a linear or branched $C_{1-5}$ alkyl group, or a linear or branched $C_{1-5}$ acyl group); Y is OH, $NR_3R_4$ ($R_3$ and $R_4$ are independently a hydrogen atom or a linear $C_{1-3}$ alkyl group, or $R_3$ and $R_4$ together form, with a nitrogen atom to which they are bonded, a 5-membered ring or a 6-membered ring that can contain a nitrogen atom or an oxygen atom as a ring constituting atom), —NHC(=NH)NHR$_5$, or —NHC(=NH)R$_5$ (where $R_5$ is a linear or branched $C_{1-5}$ alkyl group); and Z is a hydrogen atom, a linear or branched $C_{1-5}$ alkyl group, or a 5- or 6-membered ring aryl group optionally having 1 or 2 nitrogen atom(s), 1 or 2 sulfur atom(s), or 1 or 2 oxygen atom(s)].

Each substituent of the compound of Formula (I) of the present invention is described.

In the description below, n—means normal, i—means iso, sec—means secondary, t—means tertiary, Me means methyl, and Et means ethyl.

Examples of the linear or branched $C_{1-5}$ alkyl group include a methyl group, an ethyl group, an n-propyl group, an i-propyl group, an n-butyl group, an i-butyl group, a sec-butyl group, a t-butyl group, an n-pentyl group, an i-pentyl group, a sec-pentyl group, and a t-pentyl group.

Examples of the linear or branched $C_{1-5}$ acyl group include an acetyl group, a propionyl group, an n-butyryl group, an i-butyryl group, an n-pentanoyl group, an i-pentanoyl group, a sec-pentanoyl group, and a t-pentanoyl group.

Examples of the linear $C_{1-3}$ alkyl group include a methyl group, an ethyl group, and an n-propyl group.

Examples of the 5-membered ring or the 6-membered ring that $R_3$ and $R_4$ together form with a nitrogen atom to which they are bonded and that optionally contains a nitrogen atom or an oxygen atom as a ring constituting atom include a pyrrolidine ring, a piperidine ring, a morpholine ring, and a piperazine ring.

Specific examples of the 5- or 6-membered ring aryl group optionally having 1 or 2 nitrogen atom(s), 1 or 2 sulfur atom(s), or 1 or 2 oxygen atom(s) include a phenyl group, a pyridyl group, a thiazolyl group, an oxazolyl group, an imidazolyl group, a furyl group, and a thienyl group.

Next, specific examples of the substituents X, Y, and Z in the compound of Formula (I) of the present invention are shown.

Specific examples of X include a hydroxy group (OH), a methoxy group, an ethoxy group, an acetoxy group, a propionyloxy group, an amino group, a methylamino group, a dimethylamino group, an ethylamino group, a diethylamino group, an acetylamino group, and a propionylamino group.

Preferred examples of X include a hydroxy group (OH).

Specific examples of Y include a hydroxy group (OH), an amino group, a methylamino group, a dimethylamino group, an ethylamino group, a diethylamino group, a pyrrolidyl group, a piperidyl group, a morpholyl group, a piperazyl group, —NHC(=NH)NH$_2$, —NHC(=NH)NHMe, —NHC(=NH)NHMe$_2$, —NHC(=NH)NHEt, —NHC(=NH)NEt$_2$, —NHC(=NH) Me, and —NHC(=NH)Et.

Preferred examples of Y include a hydroxy group (OH).

Specific examples of Z include a hydrogen atom, a methyl group, an ethyl group, a phenyl group, a 2-furyl group, a 2-thienyl group, and a 2-pyridyl group.

Preferred examples of Z include a hydrogen atom.

In the compound of Formula (I) of the present invention, when Z is a group (an alkyl group or an aryl group) other than a hydrogen atom, a carbon atom to which Z is bonded is asymmetric, so that two types of diastereomers due to asymmetric carbon exist. However, these pure diastereomers and a mixture (including a racemic body) of these two types of diastereomers in an arbitrary ratio are also included in the compound of Formula (I) of the present invention.

The compound of Formula (I) of the present invention may be in a free form, in a form of a pharmaceutically or veterinary-medically acceptable salt of the compound, or in a form of a pharmaceutically or veterinary-medically acceptable solvate or hydrate of the compound or the salt.

Examples of the pharmaceutically or veterinary-medically acceptable salt include mineral acid salts (such as hydrochlorides, hydrobromides, sulfates, hydrogen sulfates, nitrates, phosphates, hydrogen phosphates, and dihydrogen phosphates), organic acid salts (such as formates, acetates, propionates, succinates, malonates, oxalates, maleates, fumarates, malates, citrates, tartrates, lactates, glutamates, aspartates, picrates, and carbonates), and sulfonates (such as methanesulfonates, benzenesulfonates, and toluenesulfonates).

Among the compounds of Formula (I) of the present invention, a compound in which X and Y are a hydroxy group (OH) and Z is a hydrogen atom (a compound of Formula (10)) can be produced, for example, according to the reaction formulae below:

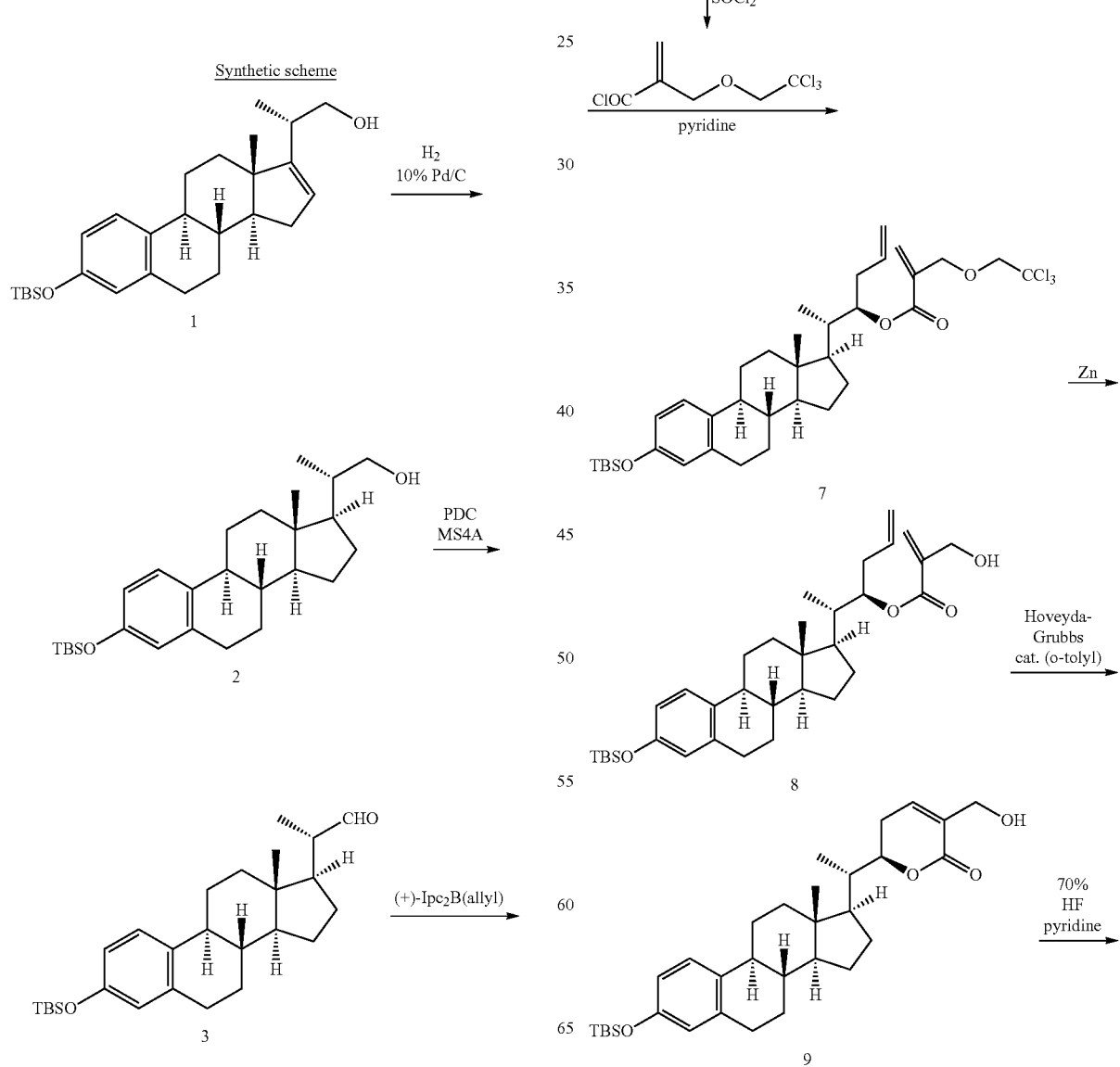

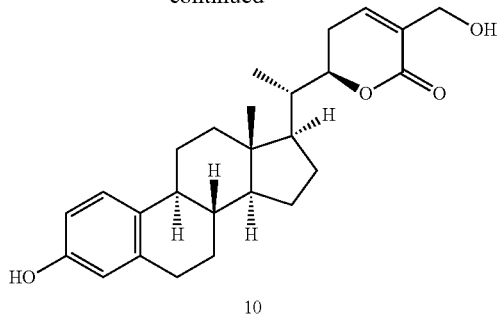

10

As the compound of Formula (1) used as a starting substance, there can be used, for example, a compound produced by a method described in a well-known document (Y. Matsuya, S. Masuda, N. Ohsawa, S. Adam, T. Tschamber, J. Eustache, K. Kamoshita, Y. Sukenaga, H. Nemoto, Eur. J. Org. Chem. (2005), p. 803-808).

Hereinafter, referring to the above-described synthetic scheme, a production method of the compound of Formula (10) is described.

By a method including: subjecting the compound of Formula (1) to a hydrogenation reaction (for example, with 10% palladium/carbon (10% Pd/C)) to reduce a double bond to prepare a compound of Formula (2); oxidizing the alcohol to an aldehyde with an oxidant such as pyridinium dichromate (PDC), for example, in the presence of a dehydrating agent such as molecular sieves 4A (MS4A) to prepare a compound of Formula (3); adding (+)-diisopinocampheylallylborane ((+)-Ipc$_2$B (allyl)), and then, adding methanol, aminoethanol, or the like to the reaction mixture to subject the compound of Formula (3) to a stereoselective allyl-boration to prepare an alcohol compound of Formula (4); reacting the alcohol compound of Formula (4) with 2-(2,2,2-trichloroethoxymethyl)acrylic acid chloride (the acid chloride can be produced, for example, by a method including: reacting sodium 2,2,2-trichloroethoxide with a compound of Formula (5) (2-(bromomethyl)acrylic acid) to prepare a compound of Formula (6) (2-(2,2,2-trichloroethoxymethyl)acrylic acid); and reacting the compound of Formula (6) with thionyl chloride or the like to prepare an acid chloride) in the presence of a base such as pyridine to prepare a compound of Formula (7); reductively breaking the 2,2,2-trichloroethoxy group with zinc or the like to prepare a compound of Formula (8); subjecting the compound of Formula (8) to a ring closure reaction with a Hoveyda-Grubbs cat. (o-tolyl) to prepare a compound of Formula (9); and subjecting the compound of Formula (9) to deprotection (elimination of t-butyldimethylsilyl group (TBS)) with 70% hydrogen fluoride/pyridine, a compound of Formula (10) can be produced.

A compound in which X is OR among the compounds of Formula (I) of the present invention can be produced, for example, by reacting a compound in which X is OH among the compounds of Formula (I) of the present invention with R-Hal (where R is the same as defined above; and Hal is a halogen atom (such as a chlorine atom and a bromine atom)) in the presence or absence of a base (such as pyridine, triethylamine, and potassium carbonate).

As a compound in which X is $NR_1R_2$ among the compounds of Formula (I) of the present invention, a compound in which $NR_1R_2$ is an amino group, a monoalkylamino group, and a dialkylamino group among the compounds in which X is $NR_1R_2$ can be produced, for example, by a method including: converting a compound in which X is OH among the compounds of Formula (I) of the present invention to a compound in which X is triflate; and reacting the resultant compound with amines (such as ammonia, monoalkylamine, and dialkylamine) in the presence of a palladium catalyst (such as palladium chloride, palladium acetate, and tetrakistriphenyl palladium).

A compound in which $R_1$ and/or $R_2$ of $NR_1R_2$ are(is) an acyl group can be produced either by reacting the above-produced compound in which $NR_1R_2$ is an amino group or a monoalkylamino group with $R_6$-Hal (where Hal is the same as defined above; and $R_6$ is a $C_{1-5}$ acyl group) in the presence or absence of a base (such as pyridine, triethylamine, and potassium carbonate), or by dehydration-condensing the above-produced compound in which $NR_1R_2$ is an amino group or a monoalkylamino group with $R_6$—OH in the presence of a dehydrating agent (such as DCC).

A compound in which Y is OH and Z is an alkyl group or an aryl group among the compounds of Formula (I) of the present invention can be produced, for example, by a method including: oxidizing (for example, by oxidizing with PCC (pyridinium chloro-chromate) or by DMSO oxidation (such as swern oxidation)) a compound in which Y is OH and Z is a hydrogen atom (that is, —CHYZ is —CH$_2$OH) among the compounds of Formula (I) of the present invention to convert the compound into an aldehyde (that is, —CH$_2$OH→—COH); and reacting the resultant aldehyde with an alkyl metal or aryl metal (metal: such as lithium, sodium, potassium, and magnesium).

A compound in which Y is $NR_3R_4$ and Z is an alkyl group or an aryl group among the compounds of Formula (I) of the present invention can be produced by a method including: sulfonylating (for example, converting into methanesulfonyl, benzenesulfonyl, p-toluenesulfonyl, or the like) OH of the above-produced compound in which Y is OH and Z is an alkyl group or an aryl group; and reacting the resultant compound with amines (such as monoalkylamine, dialkylamine, and cyclic amine (pyrrolidine, piperidine, morpholine, piperazine)).

A compound in which Y is —NHC(=NH)NHR$_5$ or —NHC(=NH)R$_5$ and Z is an alkyl group or an aryl group among the compounds of Formula (I) of the present invention can be produced by a method including: sulfonylating (for example, converting into methanesulfonyl, benzenesulfonyl, p-toluenesulfonyl, or the like) OH of the above-produced compound in which Y is OH and Z is an alkyl group or an aryl group; azidating the resultant compound with sodium azide or the like; reducing the resultant azide to an amino group; and reacting the resultant compound, for example, with R$_5$NHCN, R$_5$C(=NH)Hal (where R$_5$ and Hal are the same as defined above), or the like.

A compound in which Y is $NR_3R_4$ and Z is a hydrogen atom among the compounds of Formula (I) of the present invention can be produced by a method including: sulfonylating (for example, converting into methanesulfonyl, benzenesulfonyl, p-toluenesulfonyl, or the like) OH of the above-produced compound in which Y is OH and Z is a hydrogen atom; and reacting the resultant compound with amines (such as monoalkylamine, dialkylamine, and cyclic amine (pyrrolidine, piperidine, morpholine, piperazine)).

A compound in which Y is —NHC(=NH)NHR$_5$ or —NHC(=NH)R$_5$ and Z is a hydrogen atom among the compounds of Formula (I) of the present invention can be produced by a method including: sulfonylating (for example, converting into methanesulfonyl, benzenesulfonyl, p-toluenesulfonyl, or the like) OH of the above-produced compound in which Y is OH and Z is a hydrogen atom; azidating the resultant compound with sodium azide or the like; reducing the resultant azide to an amino group; and reacting the resultant compound, for example, with $R_5NHCN$, $R_5C(=NH)Hal$ (where $R_5$ and Hal are the same as defined above), or the like.

The compound of Formula (I) produced by the above-described production methods can ordinarily be isolated/purified by a publicly known separation/purification means, for example, means such as concentration, extraction in a solvent, filtration, recrystallization, and various chromatography separations.

As the prophylactic agent or the therapeutic agent for a neurodegenerative disease, a compound not only inhibiting the death of a neuron, but also outgrowing a neurite of a residual neuron to normalize the information transfer between neurons, is desired and the compound of Formula (I) has a neuron death-inhibiting activity and a neurite-outgrowing activity, so that the compound of Formula (I) is useful as an active ingredient of a medicine for the prevention and/or the treatment of a neurodegenerative disease related to the death of a neuron or the atrophy of a neurite. Although the neurodegenerative disease to which the medicine of the present invention can be applied is not particularly limited, examples thereof include Alzheimer's disease, cerebrovascular dementia, senile dementia, frontotemporal dementia, Lewy body dementia, Parkinson's disease, Huntington's chorea, neurogenic bladder, overactive bladder, bladder neurosis, impending incontinence, reflex incontinence, overflow incontinence, amyotrophic lateral sclerosis, cerebral hemorrhage, cerebral infarction, brain tumor, brain damage, spinal cord injury, Down's syndrome, and hyperactivity disorder.

As an active ingredient of the medicine provided by the present invention, a substance selected from a group consisting of a compound of Formula (I), a pharmaceutically or veterinary-medically acceptable salt of the compound, and a pharmaceutically or veterinary-medically acceptable solvate or hydrate of the compound or the salt, can be used.

The medicine, the prophylactic agent or the therapeutic agent for a neurodegenerative disease, and the neurite-outgrowing agonist of the present invention contain the above substance in a content of about 0.01% to 99.5%, preferably about 0.1% to 30%, based on the total mass of the composition.

The medicine, the prophylactic agent or the therapeutic agent for a neurodegenerative disease, and the neurite-outgrowing agonist of the present invention can also contain, in addition to the above substance, other pharmaceutically or veterinary-medically active compounds.

Although the clinical dose of the above substance varies depending on the age, the body weight, the sensitiveness of a patient, the degree of the symptom, or the like, an effective dose is normally around 0.05 mg to 2 g, preferably around 0.1 mg to 1 g for adults per day. However, if necessary, an amount out of the above range can also be used.

The administration route of the medicine, the prophylactic agent or the therapeutic agent for a neurodegenerative disease, and the neurite-outgrowing agonist of the present invention is not particularly limited and may be any one of oral administration or parenteral administration (such as intramuscular administration, intravenous administration, intraperitoneal administration, mucosal administration to a nasal cavity, percutaneous administration, and inhalation administration).

A substance selected from a group consisting of the compound of Formula (I), a pharmaceutically or veterinary-medically acceptable salt of the compound, and a pharmaceutically or veterinary-medically acceptable solvate or hydrate of the compound or the salt is converted into a preparation for administration by common means of preparation. That is, a tablet, a capsule, a granule, and a pill for oral administration are prepared by adding, to the above selected substance, an excipient such as sucrose, lactose, glucose, starch, and mannitol; a binder such as hydroxypropylcellulose, syrup, gum arabic, gelatin, sorbit, traganth, methylcellulose, and polyvinyl pyrrolidone; a disintegrant such as starch, carboxymethylcellulose or a calcium salt thereof, fine crystal cellulose, and polyethylene glycol; a lubricant such as talc, magnesium stearate or calcium stearate, and silica; or a lubricating agent such as sodium lauryl sulfate and glycerol.

An injection drug, a liquid drug, an emulsion, a suspension, a syrup, and an aerosol are prepared by adding, to the above selected substance, a solvent of an active ingredient such as water, ethyl alcohol, isopropyl alcohol, propylene glycol, 1,3-butylene glycol, and polyethylene glycol; a surfactant such as sorbitan aliphatic acid ester, polyoxyethylene sorbitan aliphatic acid ester, polyoxyethylene aliphatic acid ester, polyoxyethylene ether of hydrogenated castor oil, and lecithin; a suspension such as a carboxymethyl sodium salt, a cellulose derivative such as methylcellulose, traganth, and natural rubbers such as gum arabic; or a preservative such as an ester of para-oxy benzoic acid, benzalkonium chloride, and a sorbate.

For an ointment that is a percutaneous absorption-type preparation, for example, a white vaseline, a liquid paraffin, a higher alcohol, a macrogol ointment, a hydrophilic ointment, or an aqueous gel base is used. A suppository is prepared by adding, to the above selected substance, for example, cacao butter, polyethylene glycol, lanolin, aliphatic acid triglyceride, coconut oil, or polysorbate.

As a dosage form for percutaneous administration, a patch drug can also be adopted.

The patch drug may be, depending on the application thereof, in a form of various patch drugs such as a cataplasm, a plaster drug, and a tape drug.

The patch drug can be produced, for example, by a method including: adding a predetermined amount of the compound of the present invention or a pharmaceutically or veterinary-medically acceptable salt of the compound in a form suitable for applying (for example, an ointment form) to an appropriate base (for example, an aqueous base or a rubber-based base); applying the resultant mixture on an appropriate supporter in a predetermined thickness; coating the resultant laminate with a predetermined liner; and cutting the resultant laminate into a desired size. The patch drug may be formed, depending on the production method thereof, for example, by a method including: applying a base containing the compound of the present invention or a pharmaceutically or veterinary-medically acceptable salt of the compound to a liner first to form a base layer; coating the base layer with a supporter; and transferring the base layer on the supporter.

As the aqueous base or the rubber-based base, for example, an aqueous base produced by mixing the components below, can be used.

I. Aqueous Base
Component 1): water soluble polymer
Component 2): crosslinker
Component 3): polyhydric alcohol
II. Rubber-Based Base
Component 4): rubber-based polymer
Component 5): plasticizer
Component 6): adhesion imparting agent Hereinafter, Component 1) to Component 6) are described.

Examples of the water soluble polymer, which is Component 1), include polyacrylic acid, polyacrylate, polyacrylic acid partially neutralized compound, polyacrylamide, polyethyleneimine, polyvinyl alcohol, polyvinyl pyrrolidone, carboxyvinyl polymer, methylcellulose, carboxymethylcellulose, carboxymethylcellulose sodium, hydroxyethylcellulose, acrylic acid starch, vinyl ethyl acetate, gelatin, starch, eudragit, alginic acid, sodium alginate, and traganth. These water soluble polymers may be used singly or in an appropriate combination of two or more types thereof in a predetermined ratio. The blending amount of the water soluble polymer is 1 to 20% by mass, preferably 3 to 6% by mass, based on the total mass of the water soluble base.

As the crosslinker, which is Component 2), for example, salts forming a divalent or trivalent metal ion when they are dissolved in water or the like can be used. Examples of the crosslinker include a hydroxide such as aluminum hydroxide and aluminum magnesium hydroxide; a salt of an inorganic acid or an organic acid such as aluminum chloride, aluminum sulfate, dihydroxyaluminum aminoacetate, kaolin, aluminum stearate, magnesium hydroxide, magnesium chloride, and magnesium sulfate; a basic salt thereof; a double salt such as aluminum alum; an aluminic acid salt such as sodium aluminate; an inorganic aluminum complex salt and an organic aluminum chelate compound; synthesized hydrotalcite; magnesium metasilicate aluminate; magnesium silicate aluminate; aluminum nitrate; aluminum sulfate; EDTA-aluminum; aluminum allantoinate; aluminum acetate; and aluminum glycinal. These crosslinkers may be used singly or in an appropriate combination of two or more types thereof in a predetermined ratio. The blending amount of the crosslinker is 0.01 to 20% by mass, preferably 0.1 to 10% by mass, based on the total mass of the water soluble base.

The salts forming a divalent or trivalent metal ion as the crosslinker may be easily soluble in water or hardly soluble in water. When, as the crosslinker, an aluminum compound hardly soluble in water is used, a reaction rate controlling agent can be added in a reaction system in which gelation is to be performed, and particularly, by adding an acid, the reaction rate of gelation can be enhanced. By adding, as the acid, particularly an organic acid containing a hydroxy group or salts thereof, the rate of the gelation reaction is extremely enhanced. Examples of the reaction rate controlling agent include an organic acid, a salt of an organic acid, and an organic base that have a chelate forming ability or a coordination ability relative to a metal ion such as citric acid, lactic acid, tartaric acid, gluconic acid, glycolic acid, malic acid, fumaric acid, methasulfonic acid, maleic acid, acetic acid, EDTA-disodium, urea, triethylamine, and ammonia; and an inorganic acid such as hydrochloric acid, phosphoric acid, sulfuric acid, nitric acid, and hydrobromic acid.

Examples of the polyhydric alcohol, which is Component 3), include ethylene glycol, propylene glycol, trimethylene glycol, 1,3-butanediol, ethylene glycol monobutyl ether, triethylene glycol, 1,4-butanediol, glycerin, trioxyisobutane, erythrit, pentaerythrit, xylit, adonite, allodulcit, sorbitol, sorbit liquid, mannitol, and polyethylene glycol. These polyhydric alcohols may be used singly or in an appropriate combination of two or more types thereof in a predetermined ratio. The blending amount of the polyhydric alcohol is 10 to 80% by mass, preferably 10 to 60% by mass, based on the total mass of the base.

Examples of the rubber-based polymer, which is Component 4), include a styrene-isoprene-styrene block copolymer, a styrene-butadiene block copolymer, polyisobutylene, a natural rubber, polyisoprene, and polybutene. These rubber-based polymers may be used singly or in an appropriate combination of two or more types thereof in a predetermined ratio. The blending amount of the rubber-based polymer is 10 to 70% by mass, preferably 20 to 50% by mass, based on the total mass of the base.

Examples of the plasticizer, which is Component 5), include a liquid paraffin, a vegetable oil, an animal oil, polybutene, a low molecular weight polyisobutylene, vaseline, lanolin, and a higher aliphatic ester. These plasticizers may be used singly or in an appropriate combination of two or more types thereof in a predetermined ratio. The blending amount of the plasticizer is 10 to 70% by mass, preferably 20 to 50% by mass, based on the total mass of the base.

Examples of the adhesion imparting agent, which is Component 6), include a petroleum resin, a rosin-based resin, a hydrogenated rosin, ester gum, a terpene resin, a modified terpene resin, an aromatic hydrocarbon resin, and an aliphatic hydrocarbon resin. These adhesion imparting agents may be used singly or in an appropriate combination of two or more types thereof in a predetermined ratio. The blending amount of the adhesion imparting agent is 5 to 50% by mass, preferably 10 to 30% by mass, based on the total mass of the base.

The supporter used in a percutaneous absorption patch drug is not particularly limited, and as the supporter for a percutaneous absorption patch drug, a commonly used material can be used. For example, the supporter may be a woven cloth, a nonwoven cloth, a sheet, a film, or a laminate thereof of a natural or synthetic polymer. Preferred examples of the synthetic polymer include a polyvinyl chloride resin, a polyethylene-based resin (such as a polyethylene resin and a blend of a polyethylene resin with another resin), an ethylene-based copolymer resin (such as a copolymer of ethylene with another monomer), a polypropylene-based resin (such as a polypropylene resin and a blend of a polypropylene resin with another resin), and a polyurethane resin. The size, form, thickness, and the like of the supporter are accordingly selected.

The liner used in the percutaneous absorption patch drug is not particularly limited, and as the liner for the percutaneous absorption patch drug, a commonly used material can be used. For example, the liner may be a sheet, a film, or a laminate thereof of a natural or synthetic polymer. Preferred examples of the liner include a sheet, a film, and a laminate thereof of a peeling paper produced by subjecting a paper to treatment for making it easy to be peeled (for example, coating with a synthetic polymer), cellophane, polyethylene, polyethylene terephthalate, polypropylene, polyester, polyvinylidene chloride, and the like.

As the base layer in the percutaneous absorption patch drug, there can be used a base layer produced by forming a base containing, in addition to 0.1 to 30% by mass of the compound of the present invention or a pharmaceutically or veterinary-medically acceptable salt of the compound, if necessary, for example, a predetermined amount of Component 1) to Component 6), in a laminate-shape having a predetermined thickness.

In the patch drug, besides the compound of the present invention or a pharmaceutically or veterinary-medically acceptable salt of the compound and Component 1) to Component 6), if necessary, various drugs commonly used in a conventional percutaneous absorption preparation or percutaneous absorption patch drug, that is, a percutaneous absorption accelerator, an adhesion imparting agent, a softener, an antioxidant, an anti-aging agent, a preservative, a flavor, a pH adjuster, an emulsifier, a dispersant, a stabilizer, an antiseptic, an excipient, a dissolving agent, and the like may be blended in a predetermined ratio.

Examples of the antioxidant include ascorbic acid, palmitic acid, hydrogen sodium sulfite, disodium edetate, 4 disodium edetate, dry sodium sulfite, citric acid, sodium citrate, tocopherol acetate, dl-α-tocopherol, potassium dichloroisocyanurate, dibutylhydroxytoluene, butylhydroxyanisole, soy bean lecithin, sodium pyrosulfite, 1,3-butylene glycol, benzotriazole, pentaerythryl-tetrakis[3-(3,5-di-tert-butyl-4-hydroxyphenyl)propionate], propyl gallate, and 2-mercaptobenzimidazole. These antioxidants may be used singly or in an appropriate combination of two or more types thereof in a predetermined ratio. The blending amount of the antioxidant is 0.005 to 20% by mass, preferably 0.1 to 5% by mass, based on the total mass of the base.

The percutaneous absorption accelerator is not particularly limited so long as it is a percutaneous absorption accelerator normally used for a percutaneous absorption preparation. Examples of the percutaneous absorption accelerator include an alcohol, an aliphatic acid, an aliphatic acid ester, an aliphatic acid ether, a lactic acid ester, an acetic acid ester, a terpene-based compound, a pyrrolidone derivative, an organic acid, an organic acid ester, an essential oil, a hydrocarbon, and azone or a derivative thereof. Further specific examples of the percutaneous absorption accelerator include ethanol, oleyl alcohol, lauryl alcohol, myristyl alcohol, cetyl alcohol, crotamiton, cyclodextrin, calcium thioglycolate, N-methyl-2-pyrrolidone, ethyl lactate, cetyl lactate, lactic acid, urea, l-menthol, peppermint oil, d-limonene, and dl-camphor. These percutaneous absorption accelerators may be used singly or in an appropriate combination of two or more types thereof in a predetermined ratio. The blending amount of the percutaneous absorption accelerator is 0.1 to 20% by mass, preferably 0.1 to 5% by mass, based on the total mass of the base.

Examples of the dissolving agent include n-methyl-2-pyrrolidone, crotamiton, macrogol, isopropanol, peppermint oil, propylene glycol, butylene glycol, oleyl alcohol, and isopropyl myristate. Particularly, in n-methyl-2-pyrrolidone and crotamiton, the solubility of 3-methyl-1-phenyl-2-pyrazoline-5-one is high, so that these compounds are useful as the dissolving agent.

EXAMPLES

Hereinafter, the present invention is described further in detail referring to Examples, which should not be construed as limiting the scope of the present invention.

Synthesis Example 1

Synthesis of Compound of Formula (2) (2-[3-(tert-Butyldimethylsilyloxy)-13-methyl-7,8,9,11,12,13,14,15,16,17-decahydro-6H-cyclopenta[a]phenanthren-17-yl]-propan-1-ol)

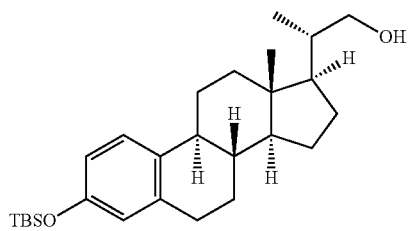

To a THF solution (60 mL) of a compound (2.61 g, 6.12 mmol) of Formula (1), 10% Pd/C (459 mg) was added, and resultant reaction mixture was filled with hydrogen and stirred at room temperature for 17 hours. Then, the reaction solution was celite-filtered and the solvent was distilled off therefrom. The resultant residue was separated by silicagel column chromatography (AcOEt:hexane=1:2) to obtain a compound of Formula (2) as a white solid substance (2.26 g, 86%, mp 88 to 90° C.).

$^1$H-NMR (300 MHz) (CDCl$_3$): δ 7.11 (1H, d, J=8.5 Hz), 6.61 (1H, dd, 8.5 Hz), 6.55 (1H, d, J=2.6 Hz), 3.67 (1H, dd, J=3.3, 10.4 Hz), 3.39 (1H, dd, J=6.9, 10.4 Hz), 2.79-2.84 (2H, m), 2.08-2.25 (3H, m), 1.83-1.89 (3H, m), 1.19-1.73 (10H, m), 1.09 (3H, d, J=6.6 Hz), 0.98 (9H, s), 0.73 (3H, s), 0.19 (6H, s); $^{13}$C-NMR (125 MHz) (CDCl$_3$): δ 153.08, 137.75, 133.19, 125.93, 119.81, 116.98, 68.04, 55.27, 52.68, 43.82, 43.27, 42.97, 39.88, 38.85, 29.77, 27.88, 27.80, 26.76, 25.79, 24.13, 18.27, 16.83, 12.22, −4.24; IR (KBr): 3358 cm$^{-1}$; MS (EI): m/z 428 (M$^+$); HRMS (EI) Calcd for C$_{27}$H$_{44}$O$_2$Si: 428.3111 (M$^+$). found: 428.3084; [α]$_D^{24.5}$=+63.76 (c=1.000, CHCl$_3$)

Here, as the compound of Formula (1), a compound synthesized according to a method described in the document below was used. (Y. Matsuya, S. Masuda, N. Ohsawa, S. Adam, T. Tschamber, J. Eustache, K. Kamoshita, Y. Sukenaga, H. Nemoto, Eur. J. Org. Chem. (2005), p. 803-808)

Synthesis Example 2

Synthesis of Compound of Formula (3) (2-[3-(tert-Butyldimethylsilyloxy)-13-methyl-7,8,9,11,12,13,14,15,16,17-decahydro-6H-cyclopenta[a]phenanthren-17-yl]-propionaldehyde)

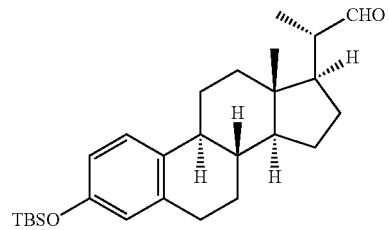

In an Ar atmosphere, to a CH$_2$Cl$_2$ (40 mL) solution of a compound (1.03 g, 2.40 mmol) of Formula (2), MS4A (444 mg) and PDC (4.51 g, 12.0 mmol) were added and the resultant reaction mixture was stirred at room temperature for 14 hours. Then, the reaction solution was celite-filtered and the solvent was distilled of therefrom. The resultant residue was separated by silicagel column chromatography (CH$_2$Cl$_2$) to obtain a compound of Formula (3) as a colorless oily substance (668 mg, 65%).

$^1$H-NMR (300 MHz) (CDCl$_3$): δ 9.60 (1H, d, J=3.3 Hz), 7.11 (1H, d, J=8.5 Hz), 6.61 (1H, dd, J=2.6, 8.5 Hz), 6.56 (1H, d, J=2.6 Hz), 2.80-2.84 (2H, m), 2.37-2.44 (1H, m), 1.20-2.35 (14H, m), 1.17 (3H, d, J=6.6 Hz), 0.98 (9H, s), 0.76 (3H, s), 0.19 (6H, s);

$^{13}$C-NMR (125 MHz) (CDCl$_3$): δ 204.84, 153.14, 137.67, 132.90, 125.91, 119.84, 117.03, 54.80, 51.24, 49.58, 43.83, 43.51, 39.71, 38.77, 29.71, 27.80, 27.22, 26.67, 25.79, 24.40, 18.27, 13.54, 12.51, −4.24; IR (neat): 1726 cm$^{-1}$; MS (EI):

Synthesis Example 3

Synthesis of Compound of Formula (4) (2-[3-(tert-Butyldimethylsilyloxy)-13-methyl-7,8,9,11,12,13,14,15,16,17-decahydro-6H-cyclopenta[a]phenanthren-17-yl]-hex-5-en-3-ol)

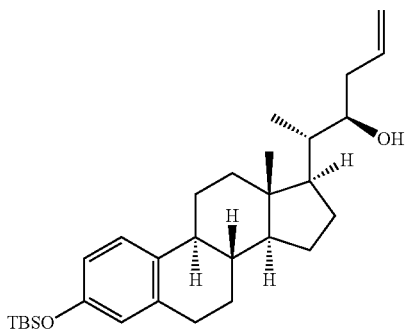

In an Ar atmosphere, to a Et$_2$O (4.5 mL) solution of a compound (382 mg, 0.896 mmol) of Formula (3), (+)-Ipc$_2$B (allyl) in pentane (1.34 mL, 1.34 mmol) was added at −78° C. and the resultant reaction mixture was stirred for 2 hours. Then, to the reaction mixture, methanol (0.36 mL, 8.88 mmol) was added and the temperature of the resultant reaction mixture was elevated to room temperature. Amino ethanol (0.53 mL, 8.66 mmol) was added to the reaction mixture and the resultant reaction mixture was stirred for 13 hours. Then, to the reaction solution, a saturated ammonium chloride aqueous solution was added and the resultant reaction mixture was extracted with CH$_2$Cl$_2$. The resultant organic phase was dried over MgSO$_4$ and was filtered, and the solvent was distilled off therefrom. The resultant residue was separated by silicagel column chromatography (CH$_2$Cl$_2$) to obtain a compound of Formula (4) as a white solid substance (348 mg, 83%, mp 107 to 108° C.).

$^1$H-NMR (300 MHz) (CDCl$_3$): δ 7.13 (1H, d, J=8.5 Hz), 6.62 (1H, dd, J=2.6, 8.5 Hz), 6.57 (1H, d, J=2.6 Hz), 5.80-5.94 (1H, m), 5.19 (1H, d, J=7.1 Hz), 5.14 (1H, s), 3.73 (1H, dt, J=2.6, 10.4 Hz), 2.80-2.85 (2H, m), 1.02-2.28 (18H, m), 1.00 (3H, d, J=6.6 Hz), 0.99 (9H, s), 0.75 (3H, s), 0.21 (6H, s); $^{13}$C-NMR (125 MHz) (CDCl$_3$): δ 153.04, 137.66, 136.15, 133.09, 125.90, 119.78, 117.69, 116.96, 72.11, 55.16, 53.36, 43.82, 43.16, 41.23, 40.01, 38.78, 34.97, 29.72, 27.80, 27.56, 26.73, 25.78, 24.09, 18.24, 12.56, 12.10, −4.27; IR (KBr): 3393, 1609 cm$^{-1}$; MS (EI): m/z 468 (M); HRMS (EI) Calcd for C$_{30}$H$_{48}$O$_2$Si: 468.3424. found: 468.3441; [α]$_D^{25.8}$=+55.09 (c=1.000, CHCl$_3$)

Synthesis Example 4

Synthesis of Compound of Formula (6) (2-(2,2,2-Trichloroethoxymethyl)acrylic acid

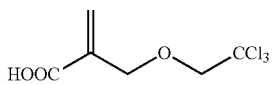

In an Ar atmosphere, to a THF (60 mL) solution of sodium hydride (60%, dispersion in paraffin liquid, 2.42 g, 60.6 mmol), 2,2,2-Trichloroethanol (5.84 mL, 60.6 mmol) was added at 0° C. and the resultant reaction mixture was stirred for 1 hour. Then, to the reaction mixture, a compound of Formula (5) (2-(Bromomethyl)acrylic acid) (2.00 g, 12.1 mmol) was added and the temperature of the resultant reaction mixture was elevated to room temperature, followed by stirring the reaction mixture for 15 hours. Then, to the reaction solution, H$_2$O was added and the reaction mixture was washed with 10% hydrochloric acid, followed by extracting the reaction mixture with saturated sodium bicarbonate water. To the resultant aqueous phase, 10% hydrochloric acid was added to make pH of the aqueous phase 3 to 4 and the aqueous phase was extracted with CH$_2$Cl$_2$. The resultant organic phase was dried over MgSO$_4$ and was filtered and the solvent was distilled off therefrom. The resultant residue (2.76 g, 98%) was confirmed to be a compound of Formula (6) by $^1$H-NMR measurement thereof and further purification of the residue was not performed, so that the residue as it was used in the next reaction.

$^1$H-NMR (300 MHz) (CDCl$_3$): δ 11.77 (1H, br), 6.53 (1H, d, J=1.4 Hz), 6.13 (1H, d, J=1.4 Hz), 4.53 (2H, d, J=1.4 Hz), 4.16 (2H, s)

Synthesis Example 5

Synthesis of Compound of Formula (7) (1-[1-(3-(tert-Butyldimethylsilyloxy)-13-methyl-7,8,9,11,12,13,14,15,16,17-decahydro-6H-cyclopenta[a]phenanthren-17-yl]-ethyl]-but-3-enyl-2-(2,2,2-trichloroethoxymethyl)-acrylate)

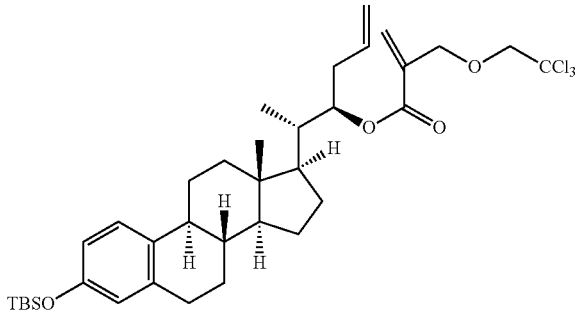

In an Ar atmosphere, to a benzene (5.0 mL) solution of a carboxylic acid (560 mg, 2.40 mmol) of Formula (6), oxalyl chloride (1.57 mL, 18.0 mmol) was added and the resultant reaction mixture was stirred at 60° C. for 1 hour. Then, benzene and excessive oxalyl chloride were distilled off therefrom. Next, in an Ar atmosphere, to a CH$_2$Cl$_2$ (10 mL) solution of an alcohol form (281 mg, 0.599 mmol) of Formula (4), pyridine (0.72 mL, 8.99 mmol) was added at room temperature, and thereto, the above prepared acid chloride was added, followed by stirring the resultant reaction mixture for 1 hour. Then, the reaction solution was diluted with CH$_2$Cl$_2$ and the resultant organic phase was washed with 10% hydrochloric acid and saturated sodium bicarbonate water in this order and was dried over MgSO$_4$. The organic phase was filtered and the solvent was distilled off therefrom. The resultant residue was separated by silicagel column chromatography (AcOEt:hexane=1:9) to obtain a compound of Formula (7) as a colorless oily substance (326 mg, 80%).

Synthesis Example 6

Synthesis of Compound of Formula (8) (1-[1-[3-(tert-Butyldimethylsilyloxy)-13-methyl-7,8,9,11,12,13,14,15,16,17-decahydro-6H-cyclopenta[a]phenanthren-17-yl]-ethyl]-but-3-enyl-2-hydroxymethylacrylate)

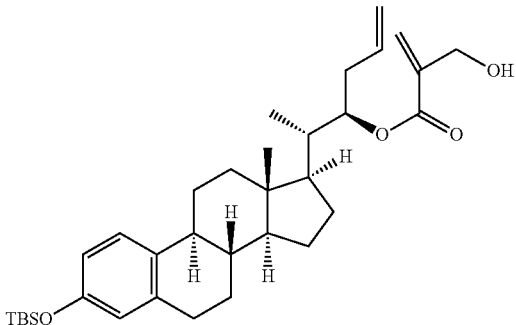

In an Ar atmosphere, to an AcOH (4.0 mL) solution of a compound (303 mg, 0.442 mmol) of Formula (7), Zn (434 mg) was added and the resultant reaction mixture was stirred at 80° C. for 4.5 hours. Then, the reaction solution was diluted with $CH_2Cl_2$ and the resultant organic phase was washed with saturated sodium bicarbonate water and was dried over $MgSO_4$. The organic phase was filtered and the solvent was distilled off therefrom. The resultant residue was separated by silicagel column chromatography (AcOa hexane=1:3) to obtain a compound of Formula (8) as a colorless oily substance (114 mg, 47%).

$^1$H-NMR (300 MHz) ($CDCl_3$): δ 7.11 (1H, d, J=8.5 Hz), 6.62 (1H, dd, J=2.6, 8.5 Hz), 6.56 (1H, d, J=2.6 Hz), 6.27 (1H, d, J=1.4 Hz), 5.81 (1H, d, J=1.4 Hz), 5.70-5.79 (1H, m), 5.03-5.13 (3H, m), 4.33 (2H, dd, J=14.0, 18.1 Hz), 2.80-2.85 (2H, m), 1.05-2.40 (18H, m), 1.03 (3H, d, J=6.9 Hz), 0.99 (9H, s), 0.73 (3H, s), 0.20 (6H, s); $^{13}$C-NMR (125 MHz) ($CDCl_3$): δ 165.57, 153.03, 139.57, 137.66, 134.92, 133.00, 125.86, 125.33, 119.80, 117.04, 116.95, 76.48, 62.55, 55.11, 53.23, 43.77, 43.23, 39.95, 39.14, 38.72, 32.18, 29.69, 27.75, 27.26, 26.68, 25.76, 24.03, 18.22, 13.27, 12.12, −4.29; IR (neat): 3450, 1709, 1608 $cm^{−1}$; MS (EI): ink 552 (M); HRMS (EI) Calcd for $C_{34}H_{52}O_4Si$: 552.3635 ($M^+$). found: 552.3662; $[α]_D^{25.6}$=+50.56 (c=1.000, $CHCl_3$)

Synthesis Example 7

Synthesis of Compound of Formula (9) (6-[1-[3-(tert-Butyldimethylsilyloxy)-13-methyl-7,8,9,11,12,13,14,15,16,17-decahydro-6H-cyclopenta[a]phenanthren-17-yl]-ethyl]-3-hydroxymethyl-5,6-dihydropyran-2-one)

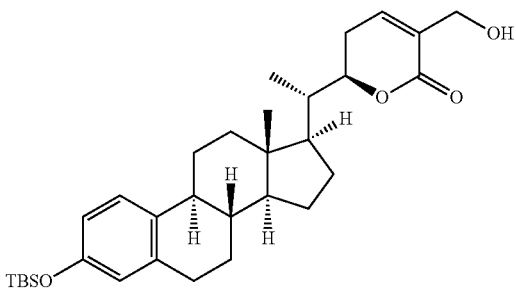

In an Ar atmosphere, to a toluene (9.0 mL) solution of a compound (49.7 mg, 0.090 mmol) of Formula (8), an improved-type Hoveyda-Grubbs catalyst (o-tolyl-type, 8.0 mg, 0.014 mmol) was added and the resultant reaction mixture was stirred at 80° C. for 1.5 hours. Then, from the reaction solution, the solvent was distilled off. The resultant residue was separated by silicagel column chromatography (AcOEt:hexane=3:2) to obtain a compound of Formula (9) as a white solid substance (26.8 mg, 57%, mp 224 to 226° C.).

$^1$H-NMR (300 MHz) ($CDCl_3$): δ 7.11 (1H, d, J=8.5 Hz), 6.86 (1H, d, J=5.8 Hz), 6.61 (1H, dd, J=2.6, 8.5 Hz), 6.55 (1H, d, J=2.6 Hz), 4.53 (1H, dt, J=3.6, 13.2 Hz), 4.32 (2H, s), 2.79-2.84 (2H, m), 2.40-2.51 (1H, m), 1.09-2.27 (17H, m), 1.07 (3H, d, J=6.6 Hz), 0.98 (9H, s), 0.75 (3H, s), 0.19 (6H, s); $^{13}$C-NMR (125 MHz) ($CDCl_3$): δ 165.84, 153.13, 140.65, 137.64, 132.87, 131.19, 125.91, 119.83, 117.03, 80.46, 61.78, 55.14, 52.21, 43.78, 43.31, 39.93, 38.96, 38.74, 29.69, 27.77, 27.47, 26.67, 25.78, 24.04, 23.16, 18.25, 13.50, 11.96, −4.25; IR (KBr): 3542, 1705, 1607 $cm^{−1}$; MS (EI): m/z 524

$^1$H-NMR (300 MHz) ($CDCl_3$): δ 7.10 (1H, d, J=8.5 Hz), 6.60 (1H, dd, J=2.6, 8.5 Hz), 6.55 (1H, d, J=2.6 Hz), 6.37 (1H, d, J=1.4 Hz), 5.97 (1H, d, J=1.4 Hz), 5.69-5.82 (1H, m), 5.00-5.15 (3H, m), 4.53 (2H, d, J=1.4 Hz), 4.15 (2H, s), 2.79-2.83 (2H, m), 1.04-2.32 (17H, m), 1.02 (3H, d, J=6.6 Hz), 0.98 (9H, s), 0.71 (3H, s), 0.19 (6H, s); $^{13}$C-NMR (125 MHz) ($CDCl_3$): δ 164.77, 153.08, 137.71, 136.57, 134.87, 133.03, 126.32, 125.90, 119.83, 116.98, 82.92, 70.88, 55.16, 53.44, 53.25, 47.63, 43.80, 43.27, 40.00, 39.22, 38.75, 32.22, 29.72, 27.78, 27.31, 26.71, 25.79, 24.06, 18.25, 16.93, 13.32, 12.15, −4.25; IR (neat): 1711, 1608 $cm^{−1}$; MS (ED: m/z 682 ($M^+$); HRMS (EI) Calcd for $C_{36}H_{53}Cl_3O_4Si$: 682.2779 ($M^+$). found: 682.2735; $[α]_D^{24.7}$=+42.16 (c=1.000, $CHCl_3$) ($M^+$); HRMS (EI) Calcd for $C_{32}H_{48}O_4Si$: 524.3322. found: 524.3353; $[α]_D^{25.4}$=+90.53 (c=1.000, $CHCl_3$)

Example 1

Synthesis of Compound of Formula (10) (6-[1-(3-hydroxy-13-methyl-7,8,9,11,12,13,14,15,16,17-decahydro-6H-cyclopenta[a]phenanthren-17-yl)-ethyl]-3-hydroxymethyl-5,6-dihydropyran-2-one)

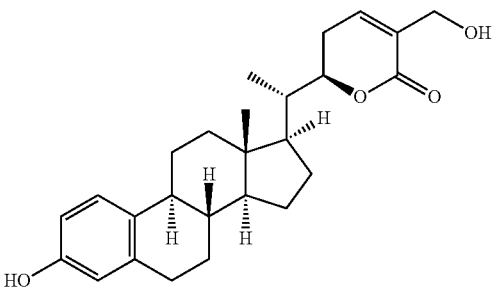

In an Ar atmosphere, to a THF (2.0 mL) solution of a compound (24.8 mg, 0.047 mmol) of Formula (9), 70% HF pyridine (drops) was added and the resultant reaction mixture was stirred at 80° C. for 30 minutes. Then, the reaction solution was diluted with $CH_2Cl_2$ and the resultant organic phase was washed with 10% hydrochloric acid and saturated sodium bicarbonate water in this order and was dried over $MgSO_4$. The organic phase was filtered and the solvent was distilled off therefrom. The resultant residue was separated by silicagel column chromatography (AcOEt) to obtain a compound of Formula (10) as a white solid substance (18.6 mg, 96%, mp 248 to 250° C.).

¹H-NMR (300 MHz) (Acetone-d₆): δ 7.08 (1H, d, J=8.2 Hz), 6.95 (1H, br), 6.59 (1H, dd, J=2.5, 8.2 Hz), 6.52 (1H, d, J=2.5 Hz), 4.39 (1H, dt, J=4.5, 11.3 Hz), 4.23-4.29 (2H, m), 2.75-2.80 (2H, m), 1.17-2.40 (19H, m), 1.06 (3H, d, J=6.9 Hz), 0.79 (3H, s); ¹³C-NMR (125 MHz) (Acetone-d₆): δ 164.98, 155.68, 139.30, 138.11, 132.49, 131.73, 126.76, 115.73, 113.38, 80.43, 60.31, 55.74, 55.36, 52.89, 44.56, 43.88, 40.64, 39.85, 31.94, 28.51, 27.81, 27.52, 24.64, 23.51, 13.69, 12.25; IR (KBr): 3470, 1690, 1617 cm⁻¹; MS (EI): m/z 410 (M⁺); HRMS (EI) Calcd for $C_{26}H_{34}O_4$: 410.2457 (M⁴). found: 410.2461; $[\alpha]_D^{30.1}$=+96.00 (c=0.910, Acetone)

Test Example: Neurite-Outgrowing Activity

1. Sample

1) Cell

Rat fetus (viviparity 17 days) cerebral cortex neuron (Sumitomo Bakelite Co., Ltd.)

Rat spinal cord dorsal root ganglion (Takara Bio Inc.)

2) Sample

Compound Produced in Example 1 (Compound of Formula (10))

3) Reagent

PNBM Basal medium (Takara Bio Inc. Cat. No. CC-3256)
PNBM NSF-1 added medium (Takara Bio Inc. Cat. No. CC-4462)
FBS (biowest, Cat. No. S1820, Lot No. S05417S1820)
mNGF2. 5S (alomone labs, PRODUCT#N-100)
Poly-L-lysine-coated cover glass 12 mm (IWAKI, Cat. No. 11-023-054)

4) Others 96-well culture plate (TPP, Cat. No. 92696)
24-well culture plate (TPP, Cat. No. 92424)
Laminin-coated: a well was coated with a culture supernatant containing laminin 5B to be used.

2. Method

1) Preparation of Neuron and Culture Conditions

Rat Fetus (Viviparity 17 Days) Cerebral Cortex Neuron

From a frozen cerebral tissue, using an attached protocol and attached reagents, a cerebral cortex neuron was prepared, was cultured in an NSF-1 (neurotrophic factor; name of substance or the like is not disclosed)-added PNBM medium for 2 hours, and then in a PNBM medium containing the sample (the compound produced in Example 1).

The dissemination was performed with a neuron concentration of 2×10⁵ cells/0.5 mL/well (24-well-plate).

Rat Spinal Cord Dorsal Root Ganglion Neuron (Spinal Cord Neuron)

A spinal cord neuron in a frozen state was thawed according to the attached protocol and the neuron was cultured in an NSF-1-added PNBM medium for 2 hours and then in a PNBM medium containing the sample (the compound produced in Example 1).

The dissemination was performed with a spinal cord neuron concentration of 2.5×10⁴ cells/0.1 mL/well (96-well-plate).

2) Preparation of Sample-Added Medium

The sample (the compound produced in Example 1) was dissolved in DMSO to prepare a 10 mM solution. The 10 mM solution was diluted with DMSO to prepare a 1 mM solution. Further dilution of the solution was performed with a PNBM medium.

Finally, sample-added media of 0.2 μM concentration and 1 μM concentration were prepared. With respect to the mNGF medium, a 5 ng/mL mNGF-added medium and a 25 ng/mL mNGF-added medium were prepared.

3. Results and Considerations

1) Investigation Using Rat Fetus (Viviparity 17 Days) Cerebral Cortex Neuron

Culture in Poly-L-Lysine-Coated Culture Vessel

Figure 2:
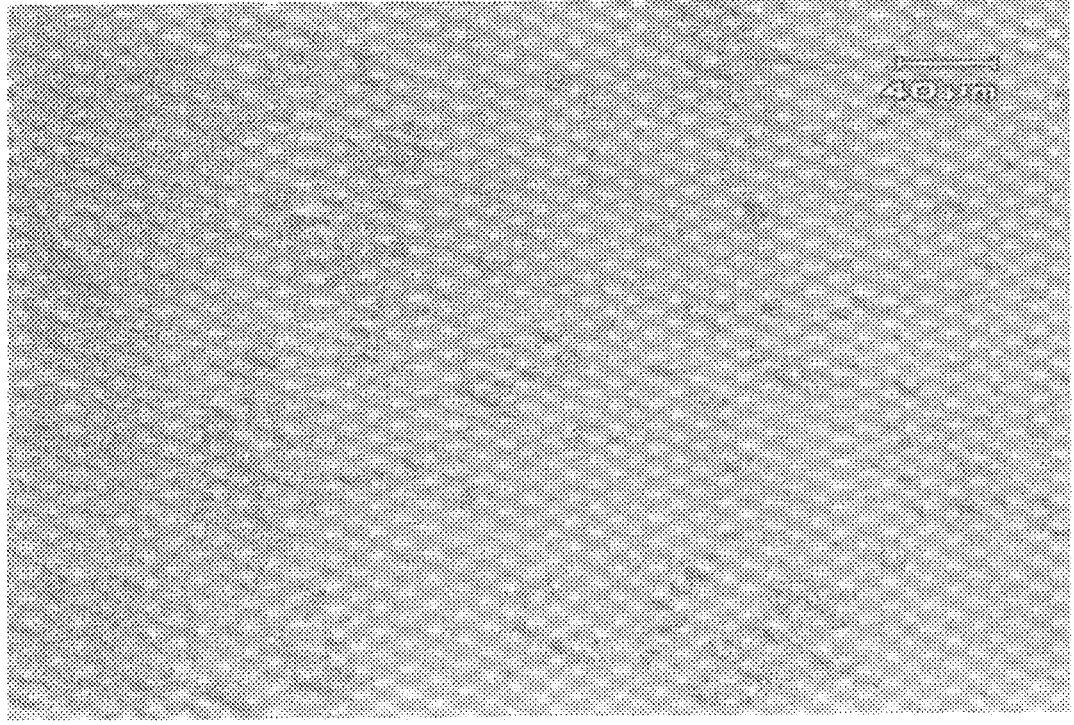
FIG. 2 is a photograph of a rat fetus cerebral cortex neuron on the second day of the culture in a neurotrophic factor (NSF-1)-added medium (in a poly-L-lysine-coated culture vessel).
Figure 3:
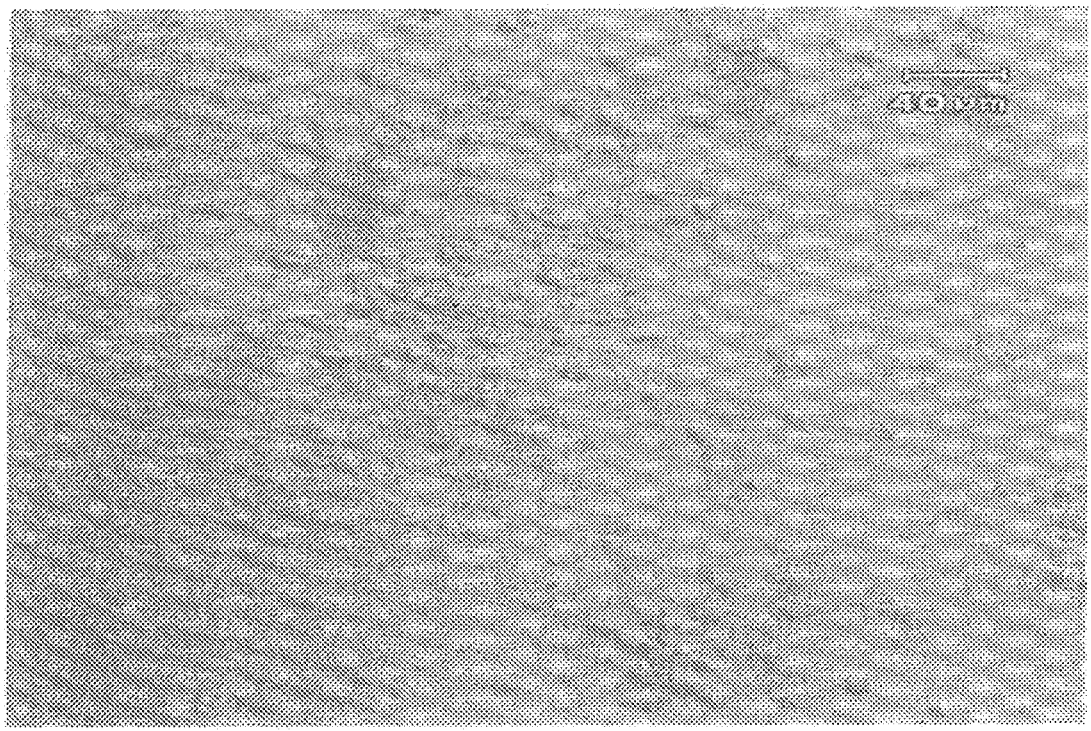
FIG. 3 is a photograph of a rat fetus cerebral cortex neuron on the second day of the culture in a sample-added medium (1 μM concentration) (in a poly-L-lysine-coated culture vessel).

A photograph of a neuron on the second day of the culture in a basal medium (additive-free) is shown in FIG. 1; a photograph of a neuron on the second day of the culture in a neurotrophic factor (NSF-1)-added medium is shown in FIG. 2; and a photograph of a neuron on the second day of the culture in a sample-added medium (1 μM concentration) is shown in FIG. 3.

Figure 4:
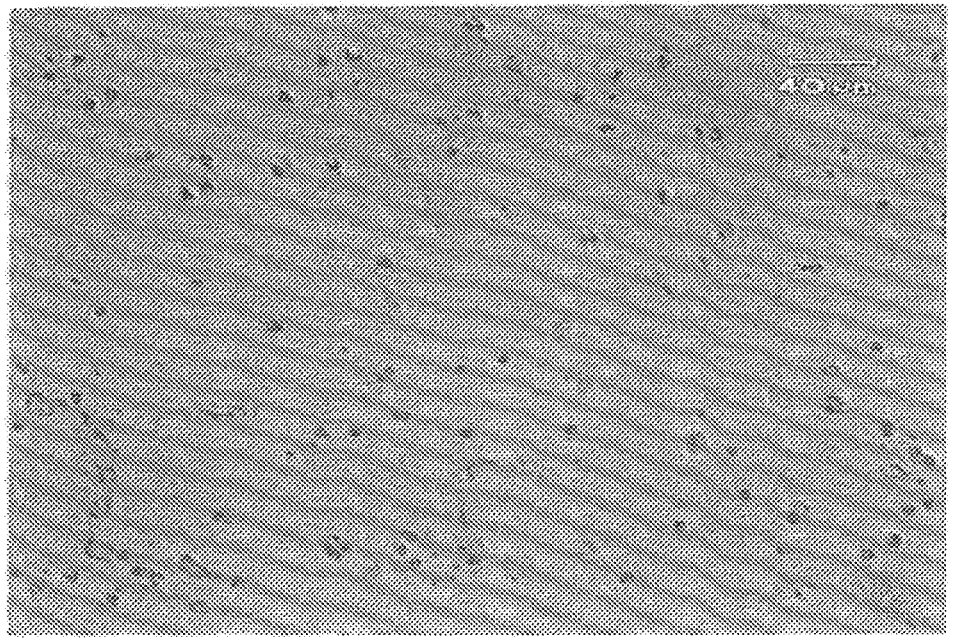
FIG. 4 is a photograph of a rat fetus cerebral cortex neuron on the fifth day of the culture in a basal medium (additive-free) (in a poly-L-lysine-coated culture vessel).
Figure 5:
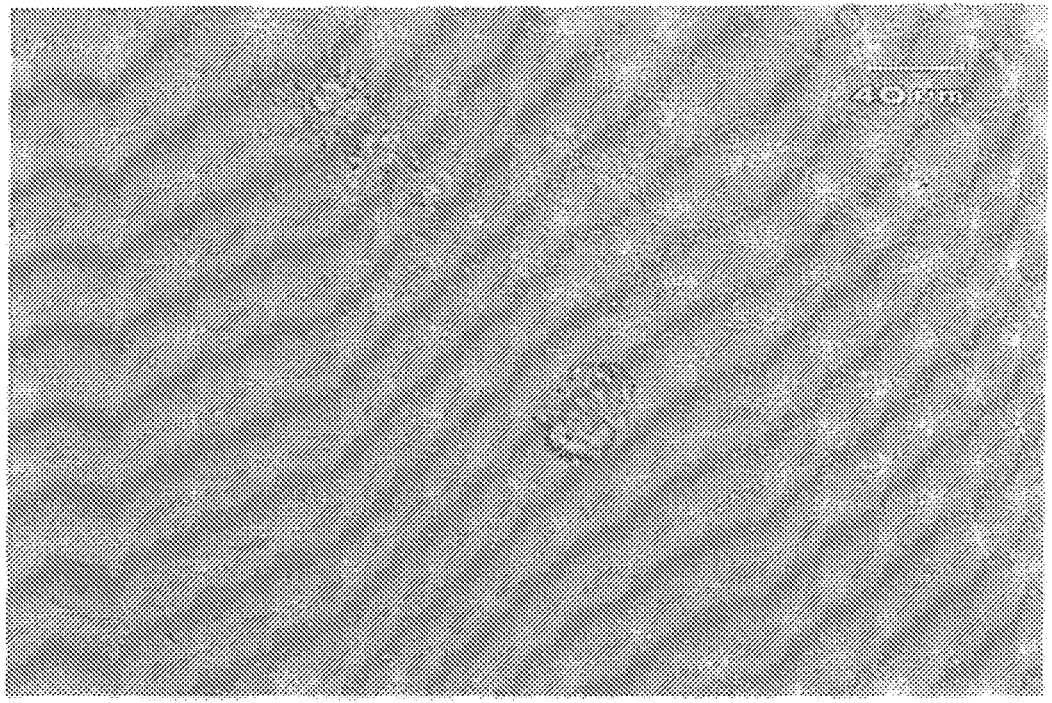
FIG. 5 is a photograph of a rat fetus cerebral cortex neuron on the fifth day of the culture in a neurotrophic factor (NSF-1)-added medium (in a poly-L-lysine-coated culture vessel).
Figure 6:
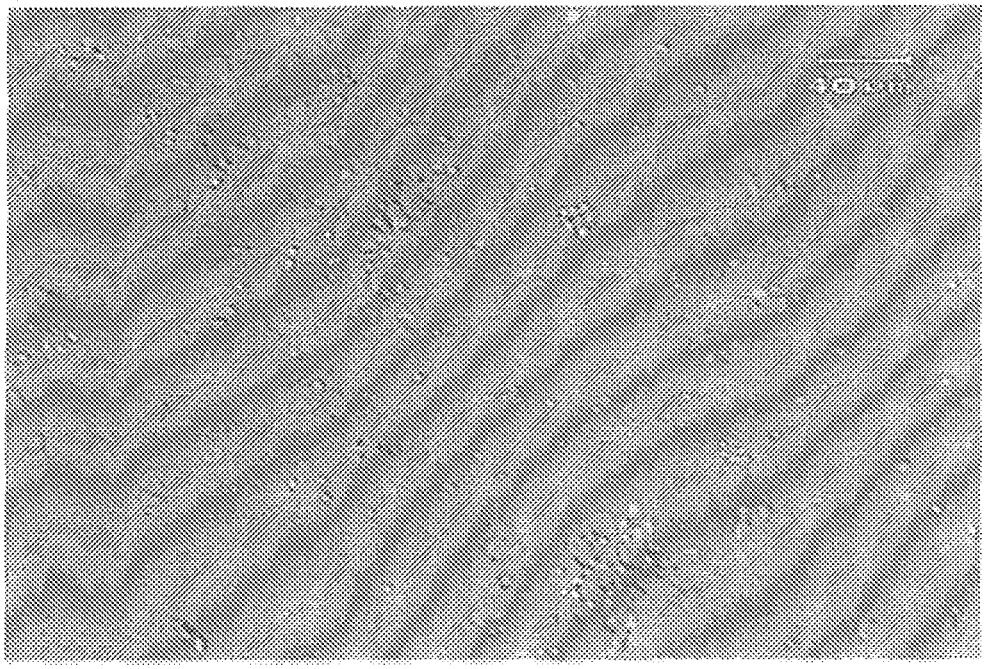
FIG. 6 is a photograph of a rat fetus cerebral cortex neuron on the fifth day of the culture in a sample-added medium (1 μM concentration) (in a poly-L-lysine-coated culture vessel).

In the neurotrophic factor (NSF-1)-added medium, the number of neurites increased apparently more than in the basal medium (additive-free). In the sample-added medium (1 μM concentration), the number of neurites increased more than in the basal medium (additive-free), but less than in the neurotrophic factor (NSF-1)-added medium. On the third day of the culture, the culture medium was exchanged. Photographs of a neuron on the fifth day of the culture are shown in the drawings (a photograph of a neuron on the fifth day of the culture in the basal medium (additive-free) is shown in FIG. 4; a photograph of a neuron on the fifth day of the culture in the neurotrophic factor (NSF-1)-added medium is shown in FIG. 5; and a photograph of a neuron on the fifth day of the culture in the sample-added medium (1 μM concentration) is shown in FIG. 6). The density, length, and thickness of a neurite are summarized in Table 1. Here, the number in Table 1 indicates a relative amount when the value in the basal medium (additive-free) is assumed to be 1.

TABLE 1

Comparison of neurite-outgrowing of rat fetus cerebral cortex neuron on the fifth day of the culture

| Sample | Neurite | | |
|---|---|---|---|
| | Density | Length | Thickness |
| Additive-free | 1 | 1 | 1 |
| NSF-1 | 3 | 2 | 2 |
| NGF 5 ng/mL | 2 | 2 | 2 |
| NGF 25 ng/mL | 2.5 | 2 | 2 |
| Example 1 (0.2 μM) | 1 | 1 | 1 |
| Example 1 (1 μM) | 1.5 | 2 | 2 |

Although the outgrowing of a neurite from a neuron did not change in the basal medium (additive-free), the outgrowing increased in other media. In the sample-added medium (1 μM concentration), the number of neurites increased less than in the neurotrophic factor (NSF-1)-added medium, but more than in the basal medium (additive-free), so that it was confirmed that the sample-added medium (1 μM concentration) has a neurite-outgrowing activity.

2) Investigation Using Rat Spinal Cord Dorsal Root Ganglion Neuron

Culture in Laminin-Coated Culture Vessel

Figure 7:
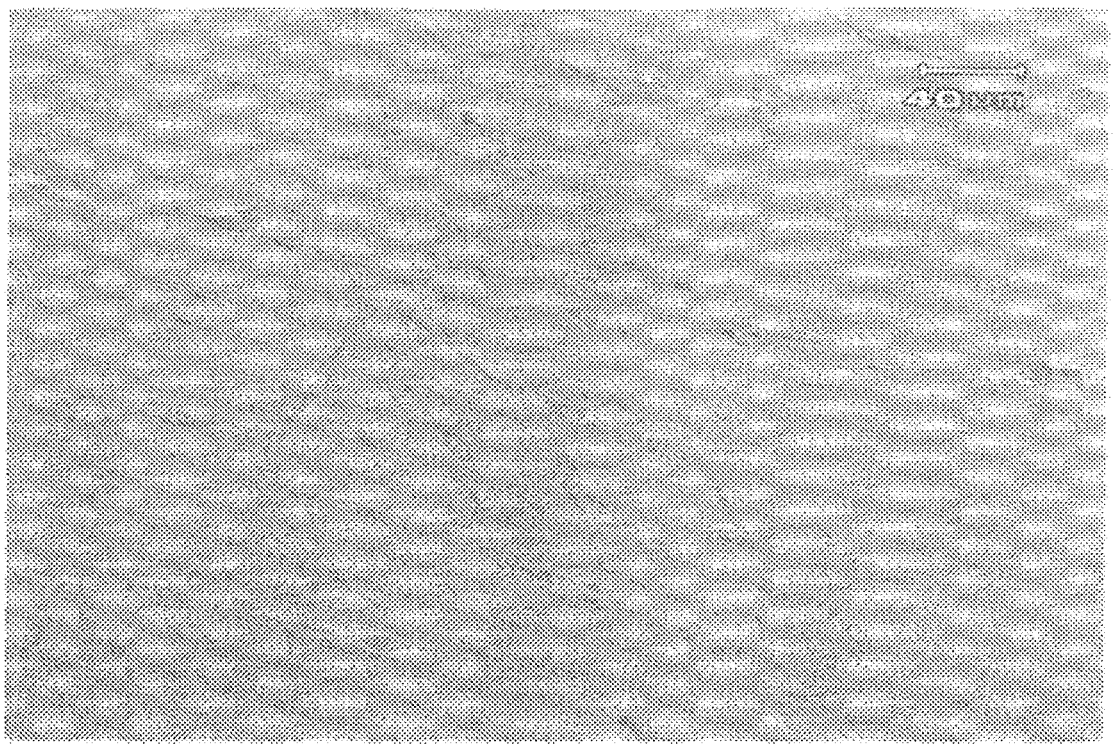
FIG. 7 is a photograph of a rat spinal cord dorsal root ganglion on the second day of the culture in a basal medium (additive-free) (in a laminin-coated culture vessel).
Figure 8:
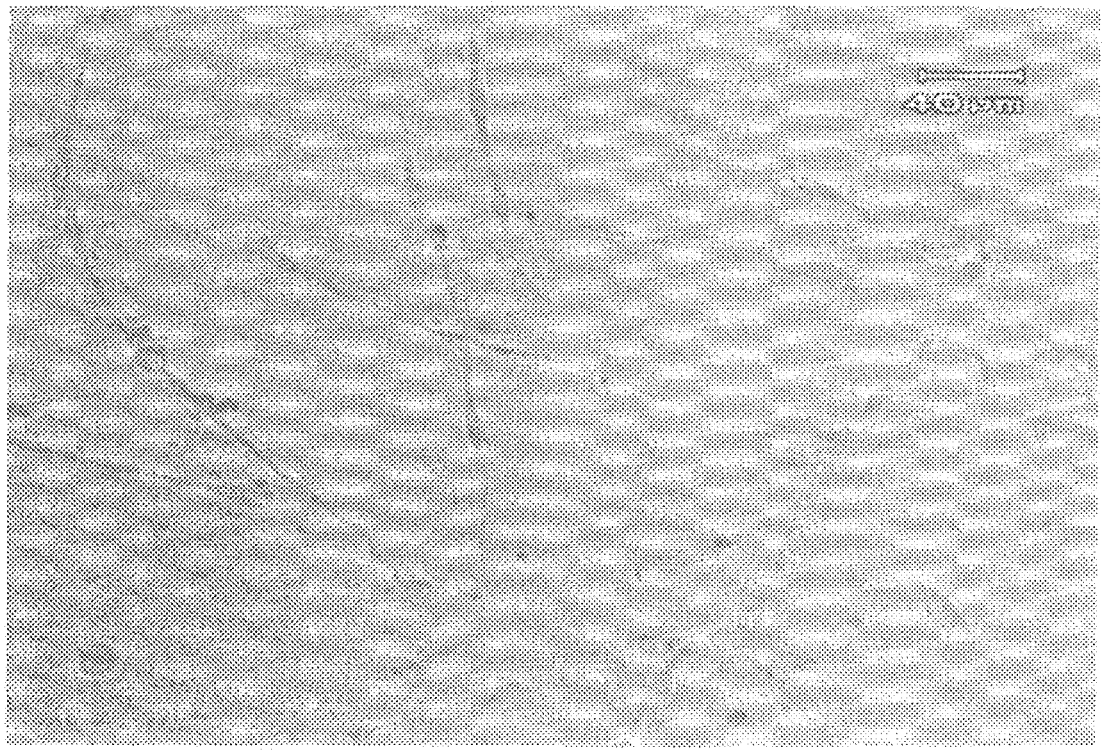
FIG. 8 is a photograph of a rat spinal cord dorsal root ganglion on the second day of the culture in a neurotrophic factor (NSF-1)-added medium (in a laminin-coated culture vessel).
Figure 9:
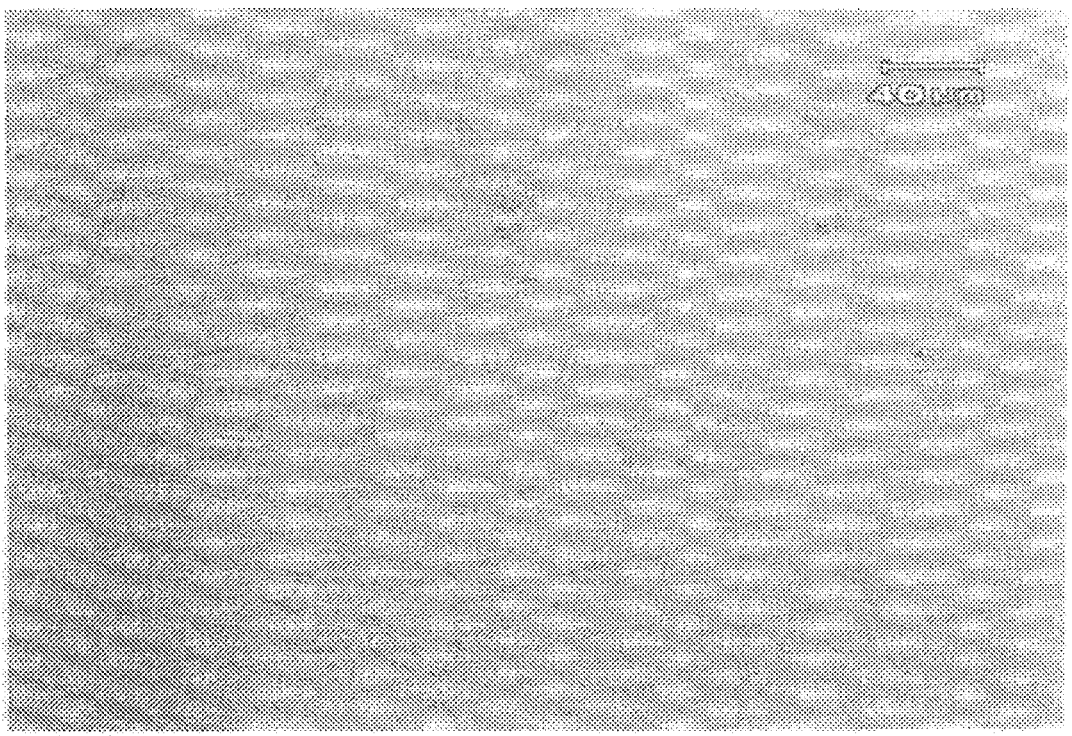
FIG. 9 is a photograph of a rat spinal cord dorsal root ganglion on the second day of the culture in a sample-added medium (1 μM concentration) (in a laminin-coated culture vessel).

A photograph of a neuron on the second day of the culture in a basal medium (additive-free) is shown in FIG. 7; a photograph of a neuron on the second day of the culture in a neurotrophic factor (NSF-1)-added medium is shown in FIG. 8; and a photograph of a neuron on the second day of the culture in a sample-added medium (1 μM concentration) is shown in FIG. 9.

A spinal cord neuron can easily outgrow a neurite (axon) and outgrows a neurite even in an additive-free medium. When as a criterion for the effect, the effect is evaluated by the length, thickness, and density of the neurite, it is apparent that in the NSF-1-added medium, the axon becomes longer.

Figure 10:
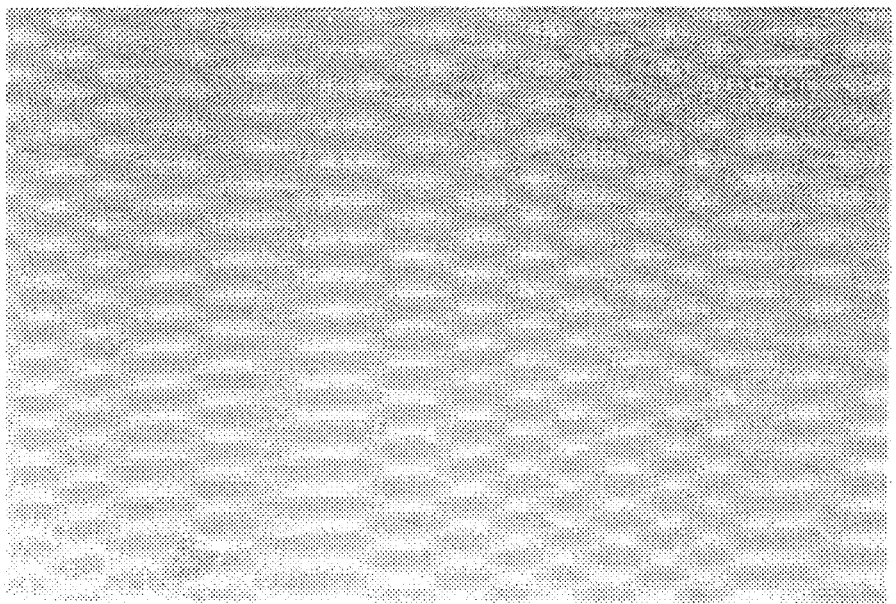
FIG. 10 is a photograph of a rat spinal cord dorsal root ganglion on the fifth day of the culture in a basal medium (additive-free) (in a laminin-coated culture vessel).
Figure 11:
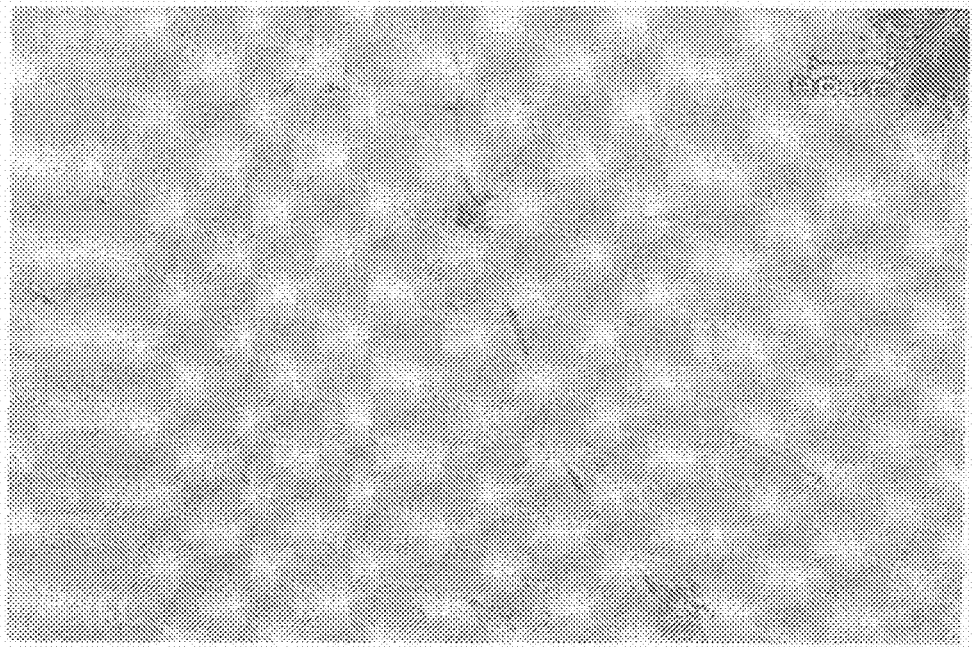
FIG. 11 is a photograph of a rat spinal cord dorsal root ganglion on the fifth day of the culture in a neurotrophic factor (NSF-1)-added medium (in a laminin-coated culture vessel).
Figure 12:
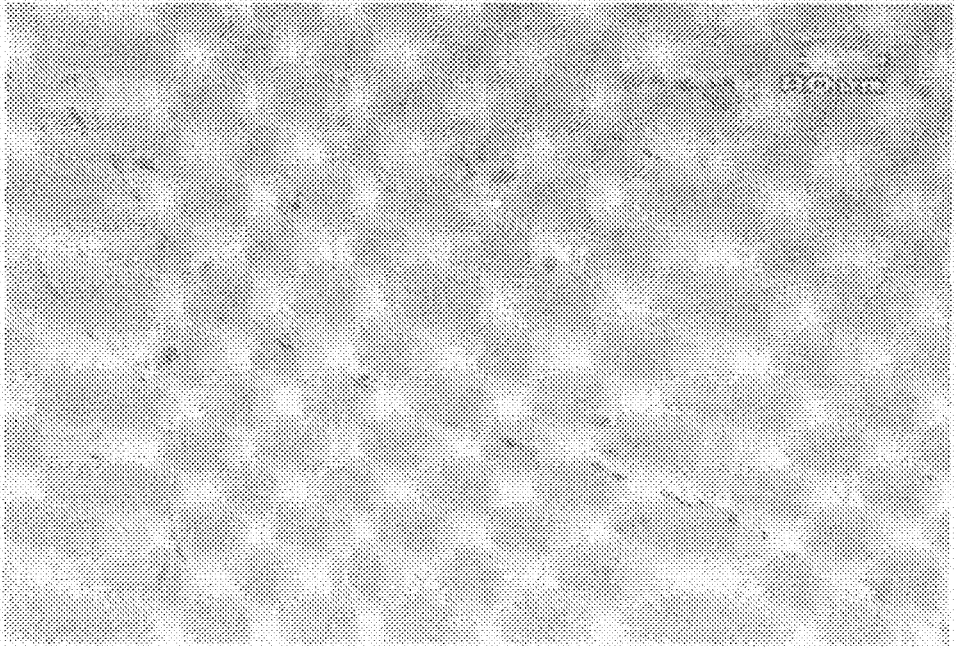
FIG. 12 is a photograph of a rat spinal cord dorsal root ganglion on the fifth day of the culture in a sample-added medium (1 μM concentration) (in a laminin-coated culture vessel).

In the sample-added medium (1 μM concentration), the axon outgrew more than in the basal medium (additive-free), but less than in the neurotrophic factor (NSF-1)-added medium. On the third day of the culture, the culture medium was exchanged. Photographs of a neuron on the fifth day of the culture are shown in the drawings (a photograph of a neuron on the fifth day of the culture in the basal medium (additive-free) is shown in FIG. 10; a photograph of a neuron on the fifth day of the culture in the neurotrophic factor (NSF-1)-added medium is shown in FIG. 11; and a photograph of a neuron on the fifth day of the culture in the sample-added medium (1 μM concentration) is shown in FIG. 12). The density, length, and thickness of a neurite (axon) are summarized in Table 2. Here, the number in Table 2 indicates a relative amount when the value in the basal medium (additive-free) is assumed to be 1.

TABLE 2

Comparison of neurite-outgrowing of rat spinal cord dorsal root ganglion neuron on the fifth day of the culture.

| Sample | Neurite | | |
| --- | --- | --- | --- |
|  | Density | Length | Thickness |
| Additive-free | 1 | 1 | 1 |
| NSF-1 | 3 | 3 | 3 |
| NGF 5 ng/mL | 2 | 2 | 1 |
| NGF 25 ng/mL | 2 | 3 | 2 |
| Example 1 (0.2 μM) | 2 | 2 | 1 |
| Example 1 (1 μM) | 2 | 2.5 | 1 |

In the neurotrophic factor (NSF-1)-added medium, the axon became thicker and longer. In the sample-added medium (1 μM concentration), however, the axon outgrew longer but did not become thicker.

4. Conclusion

From the above test, it was confirmed that the compound of the present invention has a neurite-outgrowing activity and an axon-outgrowing activity substantially comparable to those of NGF.

The invention claimed is:

1. A compound of Formula (I) or a pharmaceutically or veterinary-medically acceptable salt thereof,

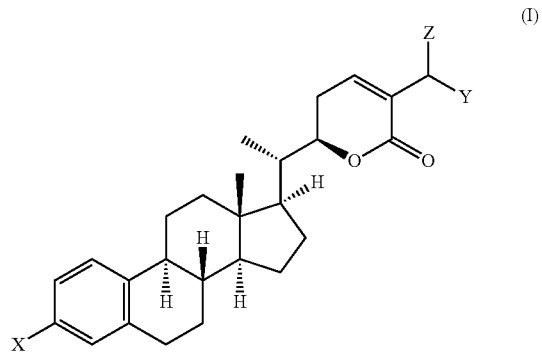

where:
X is OR;
R is a hydrogen atom, a linear or branched $C_{1-5}$ alkyl group, a linear or branched $C_{1-5}$ acyl group, or $NR_1R_2$;
$R_1$ and $R_2$ are independently a hydrogen atom, a linear or branched $C_{1-5}$ alkyl group, or a linear or branched $C_{1-5}$ acyl group;
Y is OH, $NR_3R_4$—NHC(=NH)NHR$_5$, or —NHC(=NH)R$_5$;
$R_3$ and $R_4$ are independently a hydrogen atom or a linear $C_{1-3}$ alkyl group, or $R_3$ and $R_4$ together form, with a nitrogen atom to which they are bonded, a 5-membered ring or a 6-membered ring optionally containing a nitrogen atom or an oxygen atom as a ring constituting atom,
$R_5$ is a linear or branched $C_{1-5}$ alkyl group; and
Z is a hydrogen atom, a linear or branched $C_{1-5}$ alkyl group, or a 5- or 6-membered ring aryl group optionally having 1 or 2 nitrogen atom(s), 1 or 2 sulfur atom(s), or 1 or 2 oxygen atom(s).

2. A medicinal composition comprising the compound as claimed in claim 1 or a pharmaceutically or veterinary-medically acceptable salt of the compound.

3. A method of treating a neurodegenerative disease selected from the group consisting of Alzheimer's disease, cerebrovascular dementia, senile dementia, frontotemporal dementia, Lewy body dementia, Parkinson's disease, Huntington's chorea, neurogenic bladder, overactive bladder, bladder neurosis, impending incontinence, reflex incontinence, overflow incontinence, amyotrophic lateral sclerosis, cerebral hemorrhage, cerebral infarction, brain tumor, brain damage, spinal cord injury, Down's syndrome, and hyperactivity disorder, comprising administering to a subject in need thereof the compound as claimed in claim 1 or a pharmaceutically or veterinary-medically acceptable salt of the compound.

4. A method of treating Alzheimer's disease comprising administering to a subject in need thereof the compound as claimed in claim 1 or a pharmaceutically or veterinary-medically acceptable salt of the compound.

* * * * *